US 6,676,594 B1

(12) United States Patent
Zunker et al.

(10) Patent No.: US 6,676,594 B1
(45) Date of Patent: Jan. 13, 2004

(54) C-SHAPED VAGINAL INCONTINENCE INSERT

(75) Inventors: MaryAnn Zunker, Oshkosh, WI (US); Herb F. Velazquez, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/246,005

(22) Filed: Sep. 18, 2002

(51) Int. Cl.$^7$ .................................................. A61F 2/00
(52) U.S. Cl. .......................................................... 600/29
(58) Field of Search ....................... 600/28–31; 128/885, 128/DIG. 25, 886, 846; 606/65, 67, 72, 73, 75, 232; 623/12.16

(56) References Cited

U.S. PATENT DOCUMENTS

| | | |
|---|---|---|
| 1,280,979 A | 10/1918 | Ellis |
| 1,790,801 A | 2/1931 | Dickstein |
| 2,057,206 A | 10/1936 | Pohl |
| 2,092,427 A | 9/1937 | Ross |
| 2,201,412 A | 5/1940 | Stein |
| 2,264,586 A | 12/1941 | Ross |
| 2,298,752 A | 10/1942 | Crockford |
| 2,355,628 A | 8/1944 | Calhoun |
| 2,401,585 A | 6/1946 | Seidler |
| 2,487,200 A | 11/1949 | Trager |
| 2,491,017 A | 12/1949 | Robinson |
| 2,501,972 A | 3/1950 | Seidler |
| 2,519,912 A | 8/1950 | Laun |
| 2,700,188 A | 1/1955 | Buresh et al. |
| 2,711,173 A | 6/1955 | Seidler |
| 2,739,593 A | 3/1956 | McLaughlin |
| 2,890,497 A | 6/1959 | Langdon et al. |
| 2,938,519 A | 5/1960 | Marco |
| 3,011,495 A | 12/1961 | Brecht |
| 3,032,036 A | 5/1962 | Rader et al. |

(List continued on next page.)

FOREIGN PATENT DOCUMENTS

| | | |
|---|---|---|
| BR | PI 9302334-0 A | 7/1995 |
| DE | 1815375 | 9/1970 |
| DE | 2747245 | 4/1979 |
| DE | 3122954 | 1/1983 |
| DE | 3720858 A1 | 1/1989 |
| DE | 19602878 C1 | 4/1996 |
| EP | 0460807 A2 | 12/1991 |
| EP | 0264258 B1 | 4/1992 |
| EP | 0498912 A1 | 8/1992 |
| EP | 0663197 A1 | 7/1995 |

(List continued on next page.)

OTHER PUBLICATIONS

U.S. patent application No. 09/675,459 filed Sep. 28, 2000, entitled "Urinary Incontinence Device and Method of Making Same" pp. 1–24.
U.S. patent application No. 09/675,460 filed Sep. 28, 2000, entitled "Resilient Incontinence Insert and a Method of Making the Same", pp. 1–29.

(List continued on next page.)

Primary Examiner—Eric F. Winakur
Assistant Examiner—Nikita Veniaminov
(74) Attorney, Agent, or Firm—Brinks Hofer Gilson & Lione; G. Peter Nichols

(57) ABSTRACT

A urinary incontinence device is disclosed. The device is an intra-vaginal flexible device that has a base portion connecting a proximal portion of a first leg and a proximal portion of a second leg to form a generally "C-shaped" configuration. The device also has a member that is an insertion member, a removal member, or both.

20 Claims, 4 Drawing Sheets

U.S. PATENT DOCUMENTS

| | | |
|---|---|---|
| 3,138,159 A | 6/1964 | Schmidt |
| 3,369,544 A | 2/1968 | Crockford |
| 3,409,011 A | 11/1968 | Mittag |
| 3,452,752 A | 7/1969 | Crescenzo |
| 3,469,286 A | 9/1969 | Crockford |
| 3,543,754 A | 12/1970 | Jone, Sr. |
| 3,554,184 A | 1/1971 | Habib |
| 3,596,328 A | 8/1971 | Voss |
| 3,643,661 A | 2/1972 | Crockford |
| 3,644,078 A | 2/1972 | Tachibana et al. |
| 3,646,929 A | 3/1972 | Bonnar |
| 3,705,575 A | 12/1972 | Edwards |
| 3,706,311 A | 12/1972 | Kokx et al. |
| 3,762,413 A | 10/1973 | Hanke |
| 3,765,417 A | 10/1973 | Crockford |
| 3,799,165 A | 3/1974 | Wennerblom et al. |
| 3,866,613 A | 2/1975 | Kenney et al. |
| 3,886,629 A | 6/1975 | Nakai et al. |
| 3,918,452 A | 11/1975 | Cornfield |
| 3,971,378 A | 7/1976 | Krantz |
| 3,983,875 A | 10/1976 | Truman |
| 4,011,034 A | 3/1977 | Curry et al. |
| 4,019,498 A | 4/1977 | Hawtrey et al. |
| 4,060,360 A | 11/1977 | Tapp |
| 4,074,393 A | 2/1978 | Hicklin et al. |
| 4,139,006 A | 2/1979 | Corey |
| 4,144,619 A | 3/1979 | White et al. |
| 4,148,317 A | 4/1979 | Loyer |
| 4,160,004 A | 7/1979 | Curry et al. |
| 4,160,059 A | 7/1979 | Samejima |
| 4,212,301 A | 7/1980 | Johnson |
| 4,266,546 A | 5/1981 | Roland et al. |
| 4,307,716 A | 12/1981 | Davis |
| 4,318,407 A | 3/1982 | Woon |
| 4,335,721 A | 6/1982 | Matthews |
| 4,359,357 A | 11/1982 | Friese |
| 4,398,532 A | 8/1983 | Sweeney, III |
| 4,486,191 A | 12/1984 | Jacob |
| 4,494,278 A | 1/1985 | Kroyer et al. |
| 4,498,899 A | 2/1985 | Gross |
| 4,516,570 A | 5/1985 | Taban |
| 4,536,178 A | 8/1985 | Lichstein et al. |
| 4,573,963 A | 3/1986 | Sheldon |
| 4,573,964 A | 3/1986 | Huffman |
| 4,668,557 A | 5/1987 | Lakes |
| 4,669,478 A | 6/1987 | Robertson |
| 4,823,814 A | 4/1989 | Drogendijk et al. |
| 4,857,044 A | 8/1989 | Lennon |
| 4,875,898 A | 10/1989 | Eakin |
| 4,920,986 A | 5/1990 | Biswas |
| 4,921,474 A | 5/1990 | Suzuki et al. |
| 4,973,302 A | 11/1990 | Armour et al. |
| 5,007,894 A | 4/1991 | Enhorning |
| 5,036,867 A | 8/1991 | Biswas |
| 5,041,077 A | 8/1991 | Kulick |
| 5,045,079 A | 9/1991 | West |
| 5,074,855 A | 12/1991 | Rosenbluth et al. |
| 5,080,659 A | 1/1992 | Nakanishi |
| 5,112,348 A | 5/1992 | Glassman |
| 5,147,301 A | 9/1992 | Ruvio |
| 5,224,494 A | 7/1993 | Enhorning |
| 5,273,521 A | 12/1993 | Peiler et al. |
| 5,336,208 A | 8/1994 | Rosenbluth et al. |
| 5,352,182 A | 10/1994 | Kalb et al. |
| 5,355,896 A | 10/1994 | Schulman |
| 5,386,836 A | 2/1995 | Biswas |
| 5,395,308 A | 3/1995 | Fox et al. |
| 5,395,309 A | 3/1995 | Tanaka et al. |
| 5,476,434 A | 12/1995 | Kalb et al. |
| 5,483,976 A | 1/1996 | McLaughlin et al. |
| 5,512,032 A | 4/1996 | Kulisz et al. |
| 5,533,990 A | 7/1996 | Yeo |
| 5,554,109 A | 9/1996 | Frayman |
| 5,603,685 A | 2/1997 | Tutrone, Jr. |
| 5,609,559 A | 3/1997 | Weitzner |
| 5,609,586 A | 3/1997 | Zadini et al. |
| 5,611,768 A | 3/1997 | Tutrone, Jr. |
| 5,618,256 A | 4/1997 | Reimer |
| 5,659,934 A | 8/1997 | Jessup et al. |
| 5,752,525 A | 5/1998 | Simon et al. |
| 5,755,906 A | 5/1998 | Achter et al. |
| 5,771,899 A | 6/1998 | Martelly et al. |
| 5,785,640 A | 7/1998 | Kresch et al. |
| 5,795,346 A | 8/1998 | Achter et al. |
| 5,807,372 A | 9/1998 | Balzar |
| 5,813,973 A | 9/1998 | Gloth |
| 5,816,248 A | 10/1998 | Anderson et al. |
| 5,873,971 A | 2/1999 | Balzar |
| 5,885,204 A | 3/1999 | Vergano |
| 5,894,842 A | 4/1999 | Rabin et al. |
| 5,908,379 A | 6/1999 | Schaefer et al. |
| 5,988,169 A | 11/1999 | Anderson et al. |
| 5,988,386 A | 11/1999 | Morrow |
| 6,019,743 A | 2/2000 | Cole et al. |
| 6,030,375 A | 2/2000 | Anderson et al. |
| 6,039,716 A | 3/2000 | Jessup et al. |
| 6,039,828 A | 3/2000 | Achter et al. |
| 6,056,714 A | 5/2000 | McNelis et al. |
| 6,071,259 A | 6/2000 | Steiger et al. |
| 6,090,038 A | 7/2000 | Zunker et al. |
| 6,090,098 A | 7/2000 | Zunker et al. |
| 6,095,998 A | 8/2000 | Osborn, III et al. |
| 6,142,928 A | 11/2000 | Zunker et al. |
| 6,189,535 B1 | 2/2001 | Enhorning |
| 6,248,089 B1 | 6/2001 | Porat |
| 6,270,470 B1 | 8/2001 | Buck et al. |
| 6,283,952 B1 | 9/2001 | Child et al. |
| 6,415,484 B1 | 7/2002 | Moser |
| 6,419,777 B1 | 7/2002 | Achter et al. |
| 6,460,542 B1 * | 10/2002 | James ..................... 128/885 |
| 2002/0083949 A1 | 7/2002 | James |
| 2002/0090390 A1 | 7/2002 | Mahashabde et al. |

FOREIGN PATENT DOCUMENTS

| | | |
|---|---|---|
| EP | 0363421 B2 | 10/1995 |
| EP | 0714271 B1 | 6/1996 |
| FR | 2228464 | 12/1974 |
| FR | 2342717 | 9/1977 |
| GB | 1115727 | 5/1968 |
| GB | 1116742 | 6/1968 |
| GB | 1359343 | 4/1974 |
| WO | WO 88/10106 | 12/1988 |
| WO | WO 94/13223 | 6/1994 |
| WO | WO 95/05790 | 3/1995 |
| WO | WO 95/16423 | 6/1995 |
| WO | WO 95/28139 | 10/1995 |
| WO | WO 96/10965 | 4/1996 |
| WO | WO 98/06365 | 2/1998 |
| WO | WO 98/42281 | 10/1998 |
| WO | WO 00/36996 | 6/2000 |
| WO | WO 00/37012 | 6/2000 |
| WO | WO 00/37013 | 6/2000 |
| WO | WO 02/053071 A1 | 7/2002 |
| WO | WO 02/089704 A2 | 11/2002 |

OTHER PUBLICATIONS

U.S. patent application No. 10/039,230 filed Dec. 31, 2001, entitled "Incontinence Insert Device and Method of Using Same", pp. 1–18.

U.S. patent application No. 10/245,964 filed Sep. 18, 2002, entitled "Molar Shaped Vaginal Incontinence Insert", pp. 1–16.

U.S. patent application No. 10/328,428 filed Dec. 23, 2002, entitled "Compressible Resilient Incontinence Insert", pp. 1–16.

Concert Fabricatation, Ltee, *Nonwovens Industry*, p. 1110, May, 1996.

* cited by examiner

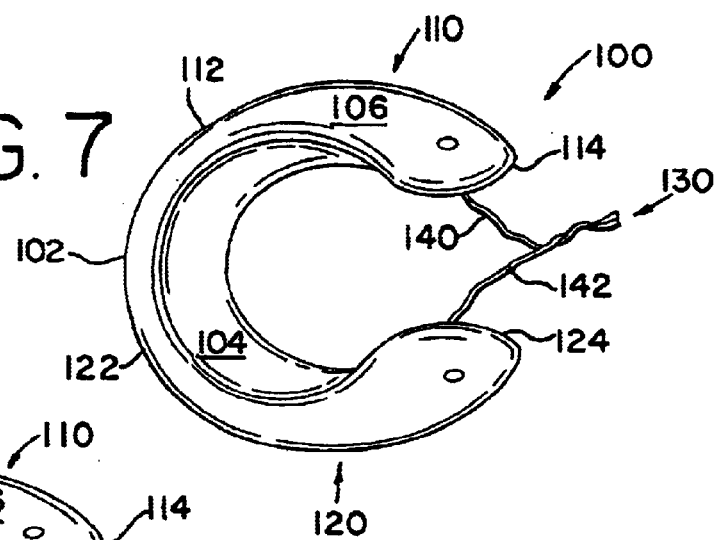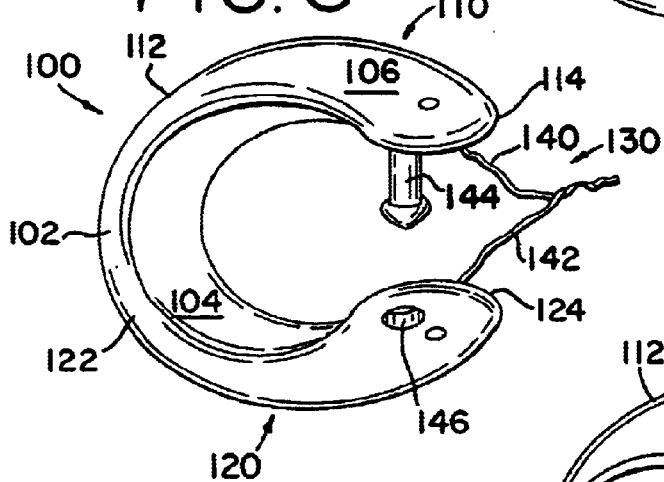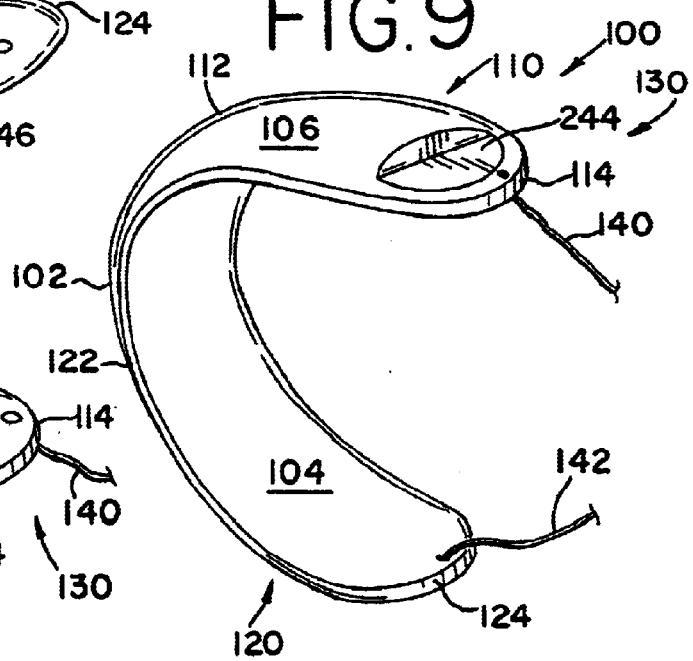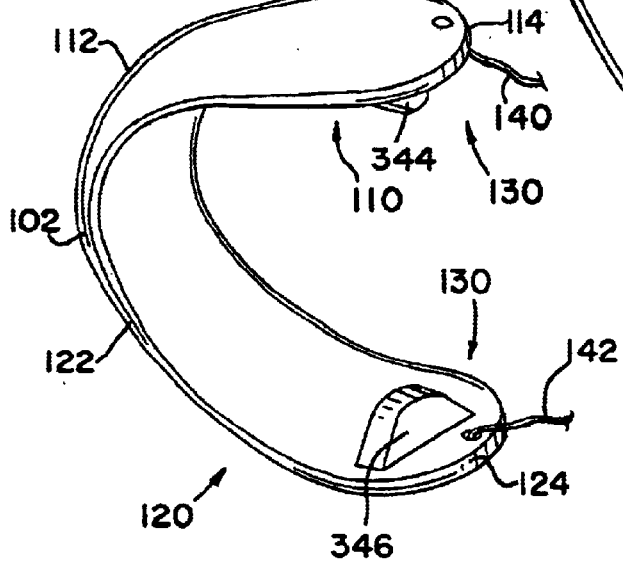

C-SHAPED VAGINAL INCONTINENCE INSERT

FIELD OF THE INVENTION

The present invention relates to a urinary incontinence device and a method of using the same. More specifically, this invention relates to a cost-effective C-shaped device for alleviating female urinary incontinence, particularly during episodes of increased intra-abdominal pressure.

BACKGROUND OF THE INVENTION

The primary etiological factor producing genuine stress urinary incontinence is the incomplete transmission of abdominal pressure to the proximal urethra due to displacement from its intra-abdominal position. Some women, especially women who have given birth to one or more children, and older women, can experience incidences of involuntary urine loss due to stress urinary incontinence or combined stress and urge incontinence. A sneeze or cough increases the intra-abdominal pressure, which in turn increases the pressure on a person's bladder causing the involuntary release of urine. The frequency and severity of such urine loss can increase as the muscles and tissues near the urethro-vaginal myofascial area grow weaker. It has also been recognized that the urinary sphincter muscle, which is located at the upper end of the urethra, adjacent to the bladder, works well at sealing off the passing of urine from the bladder to the urethra when it has a round or circular cross-sectional configuration.

Support of the proximal urethra elevates it above the pelvic floor and subjects it to increases in intra-abdominal pressure, thus allowing compression and maintenance of continence. When this passageway becomes distorted into a cross-sectional configuration having more of an elliptical or oval appearance, however, the sphincter muscle can not close properly. Therefore, the tendency for involuntary urine loss increases. One must remember that the urethra and vagina are not separate structures. Because of their common derivation from the urogenital sinus, they are fused in the distal two-thirds of the urethra. In this region they are bound together by the endopelvic connective tissue so that the support of the urethra depends not only on the attachments of the urethra itself to adjacent structures but also on the connection of the vagina and periurethral tissues to the pelvic wall.

As the world's female population ages, there is an ever-increasing need for a non-surgical method or measure to reduce the involuntary urine loss commonly associated with stress urinary incontinence. Although there are specialized products available for this purpose, most can only be purchased with a prescription and they need to be properly sized, physically inserted and/or adjusted by a medical doctor for them to correctly perform.

In view of the lack of non-prescription, commercially available devices, there is a need for a urinary incontinence device that the consumer can purchase and that is uncomplicated and user friendly. Furthermore, there is a need for a urinary incontinence device that is easy for a woman to insert into and remove from their body that is more comfortable to wear and to provide psychological and realistic assurance that it is capable of properly performing over an extended period of time.

SUMMARY OF THE INVENTION

The present invention relates to an intra-vaginal urinary incontinence device that includes a flexible base portion that connects a proximal portion of a first leg and a proximal portion of a second leg to form a generally "C-shaped" configuration. The device also includes a member selected from the group consisting of an insertion member, a removal member, or both. The device may be formed of a resilient material so that the distal portion of the legs can be moved toward each other to aid in the insertion of the device into the vaginal canal.

In addition, the base of the device may bias the legs outwardly or in a direction away from each other so that, in use, the device will be more securely retained within the vagina. Advantageously, the device may be selectively positioned within the vagina so that each of the legs may respectively contact the left vaginal wall and the right vaginal wall or the anterior vaginal wall and the posterior vaginal wall.

Because of the C-shaped configuration, the device may be inserted so that in use, the device has an upwardly convex shape with the legs extending downward. In this configuration, the member is provided on the distal end of at least one leg and typically provided on the distal end of each leg. In this regard, the member may include a first removal member provided on the distal portion of the first leg and a second removal member provided on the distal portion of the second leg. Each of the first and second removal members may include a string.

To aid the insertion of the device, the member may further include an insertion member that may be separate from the removal member or may be formed as part of the removal member. The insertion member may take any of several forms such that a first insertion member is provided on the distal portion of the first leg and a second insertion member is provided on the distal portion of the second leg.

Alternatively, the device may be inserted so that in use, the device has a downwardly concave shape with the legs extending upward. In this embodiment, the member is provided on the outer surface of the base portion of the device. The member may be integrally formed with the device and shaped to provide a surface that can be gripped for insertion and removal of the device.

Put another way, the device of the present invention is an intra-vaginal device that has a first portion to engage either an anterior vaginal wall or a left vaginal wall and a second portion to engage either a posterior vaginal wall or a right vaginal wall, respectively. The device has a generally arcuate configuration and is formed of a resilient material so that in use it may be resiliently deformed and therefore bias the first and second portions into contact with the anterior and posterior (or left and right) vaginal walls, respectively to retain the device in position within the vagina. The device also has a member connected to the base wherein the member is selected from the group consisting of an insertion member, a removal member, and a combination of both. The member may be integrally formed as part of the device.

The present invention also includes a method of alleviating female urinary incontinence by providing a female urinary incontinence device as described above and in the specification, selectively inserting the device into a woman's vagina while compressing the legs of the device toward each other, and allowing the legs of the device to expand within the vaginal canal so that each leg of the device respectively contacts the left vaginal wall and the right vaginal wall or the anterior vaginal wall and the posterior vaginal wall.

Advantageously, the device and method of present invention provides for control of female urinary incontinence by use of a device that does not create undue friction or distension of the mucosal tissue and yet allows for normal discharge of vaginal secretions.

BRIEF DESCRIPTION OF THE DRAWINGS

FIG. 7 is a perspective view of another embodiment of the urinary incontinence device of the present invention where the legs of the device are in a downward position when the device is inserted and where the member includes a removal member at the distal end of each leg.

FIG. 8 is a perspective view of another embodiment of the urinary incontinence device of the present invention where the legs of the device are in an upward position when the device is inserted and wherein the device includes a member that includes a removal member at the distal end of each leg and an insertion member for cooperating with an insertion apparatus (not shown).

FIG. 9 is a perspective view of another embodiment of the urinary incontinence device of the present invention where the legs of the device are in an upward position when the device is inserted and wherein the device includes a member that includes a removal member at the distal end of each leg and an insertion member for cooperating with an insertion apparatus (not shown).

FIG. 10 is a perspective view of another embodiment of the urinary incontinence device of the present invention where the legs of the device are in an upward position when the device is inserted and wherein the device includes a member that includes a removal member at the distal end of each leg and an insertion member for cooperating with an insertion apparatus (not shown).

DESCRIPTION OF THE INVENTION

Figure 1:
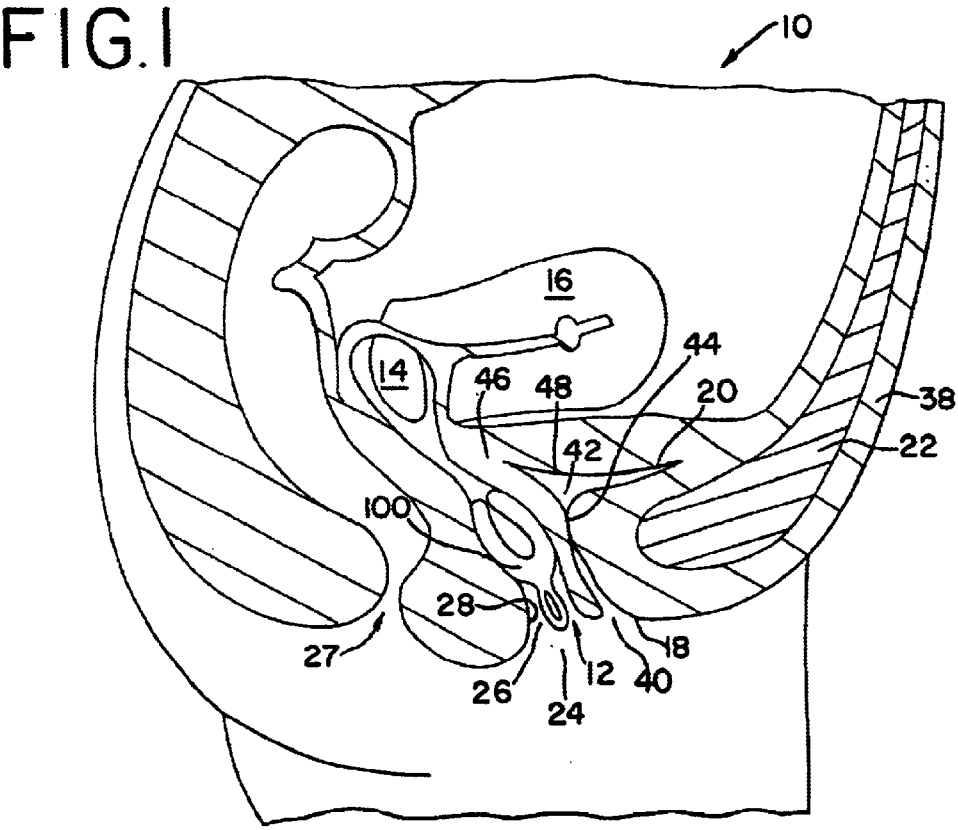
FIG. 1 is a mid-sagittal section of a human torso showing one embodiment of a urinary incontinence device positioned in the vaginal canal and cooperating with the symphysis pubis to allow the urethral tube to be compressed upon itself and alleviate urinary incontinence during episodes of increased intra-abdominal pressure.
Figure 2:
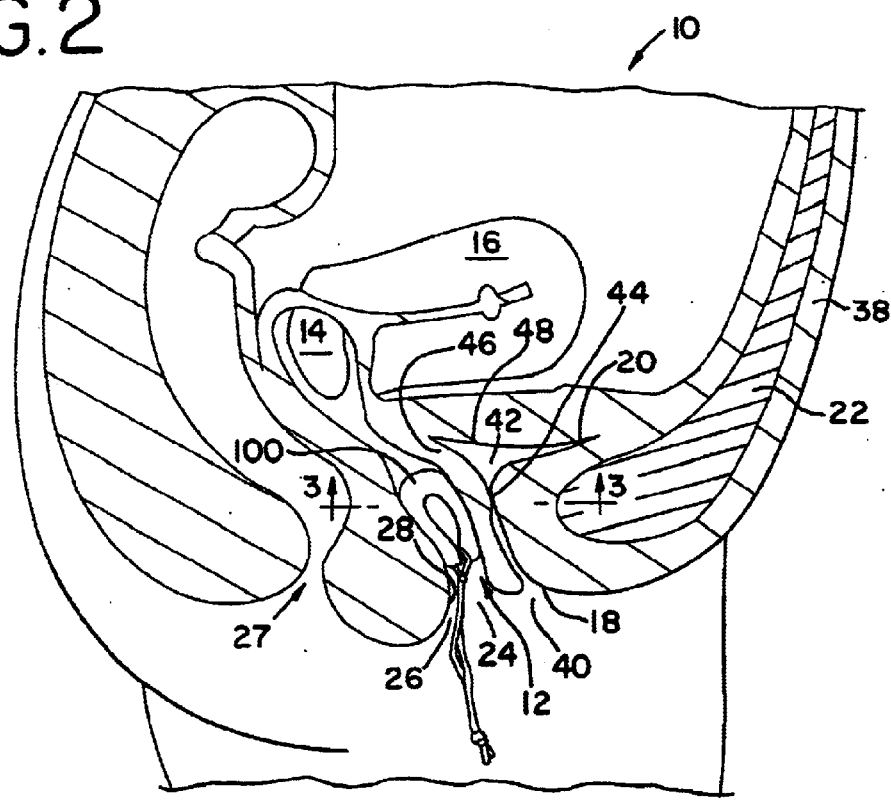
FIG. 2 is a mid-sagittal section of a human torso showing another embodiment of a urinary incontinence device positioned in the vaginal canal and cooperating with the symphysis pubis to allow the urethral tube to be compressed upon itself and alleviate urinary incontinence during episodes of increased intra-abdominal pressure.

Turning now to FIGS. 1 and 2, a human torso 10 of a female is shown with a vagina 12, a cervix 14, a uterus 16, a urethra 18, a bladder 20 and a symphysis pubis 22. The vagina 12 has an intraoital opening 24 that exits the human body 10 and contains a vaginal canal 26 that extends from the intraoital opening 24 to the cervix 14. The vaginal canal 26 has a length that ranges from between about 4 inches to about 6 inches (about 102 millimeters (mm), to about 153 mm) in most women. The cervix 14 is the entrance to the womb and is located between the upper aspect of the vaginal canal 26 and the uterus 16. The rectum 27 is located posterior to the vagina 12. The vaginal canal 26 has an inner periphery 28.

Figure 3:
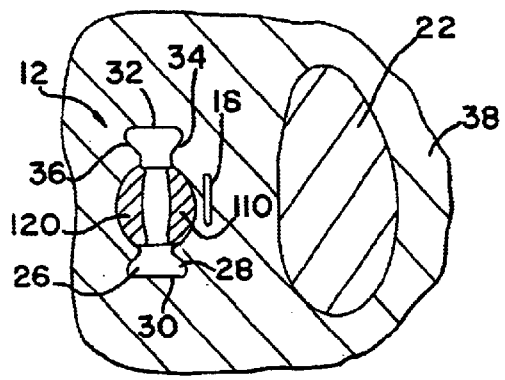
FIG. 3 is a sectional view taken along line 3—3 of FIG. 1 wherein the legs of the urinary incontinence device contact the anterior vaginal wall and the posterior vaginal wall.
Figure 4:
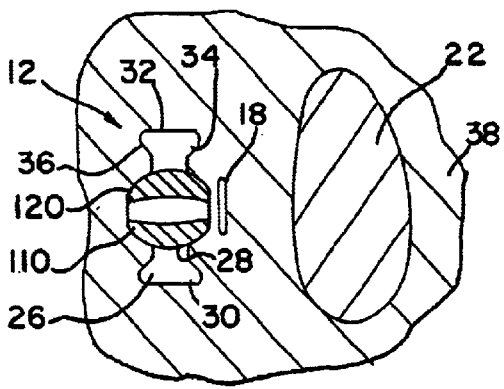
FIG. 4 is a sectional view taken along line 3—3 of FIG. 1 except that the legs of the urinary incontinence device contact the left vaginal wall and the right vaginal wall.

As best seen in FIGS. 3 and 4, the inner periphery 28 is made up of a right lateral wall 30, a left lateral wall 32. an anterior wall 34, and a posterior wall 36. The four walls 30, 32, 34, and 36 encompass the entire 360 degrees of the inner periphery 28. The anterior wall 34 is located closest to the urethra 18 and the urethra 18 is located between the symphysis pubis 22 and the vagina 12.

The vaginal canal 26 can be divided into three approximately equal sections, each representing about one-third of the overall length. Each section is approximately 2 inches (approximately 51 mm) in length. The middle third of the vaginal canal 26 is the most important section for alleviating female urinary incontinence because of its proximity to the urethra 18 and is the location where a urinary incontinence device should be positioned. The middle third of the vaginal canal 26 is also horizontally offset from the symphysis pubis 22, which is a bony prominence situated adjacent to a front portion 38 of the human torso 10. Cooperation between a urinary incontinence device positioned in the vagina 12 and the symphysis pubis 22 allows the urethra 18 to be compressed upon itself thereby alleviating involuntary urine flow from the bladder.

The urethra 18, also referred to as a urethral tube, is a hollow tube that extends from a first opening 40 that exits the human body 10 to a second opening 42 situated at the lower surface of the bladder 20. The urethra 18 has a length of about 1.5 inches (about 38 mm) in most women. The urethra functions to discharge urine, which is temporarily stored in the bladder 20, from the human body. The urethra 18 has a plurality of urethral sphincter muscles 44 located along the length of its inner periphery. The urethral sphincter muscles 44 are situated below the opening 42 and are ring like muscles that normally maintain constriction of the urethra 18 to prevent the passage of urine. The relaxation of the urethral sphincter muscles 44 by normal physiological functioning will permit urine to be voluntarily expelled from the body.

Again, referring to FIGS. 1 and 2, the human torso 10 further includes musculature and body tissue located in the urethrovaginal myofascial area 46 that is situated between the vagina 12 and the symphysis pubis 22. The bladder 20 lies posterior to the symphysis pubis 22 and is separated from the rectum 27 by the vagina 12 and the uterus 16. The ureters (not shown) that transport urine from the kidneys to the bladder 20, pass from the pelvis to the posterior aspect of the urinary bladder 20. The fundus vesicae 48, into which both of the ureters terminate, is located adjacent to the anterior wall 34 of the vagina 12.

Referring to FIGS. 1 and 2, a urinary incontinence device 100 is shown positioned in the vaginal canal 26. The urinary incontinence device 100 is designed to bridge across the vagina to support the musculature and body tissue located in the urethra-vaginal myofascial area 46.

In FIGS. 3 and 4, the urinary incontinence device 100 is shown in an expanded state. A portion of the urinary incontinence device 100 and, in particular, the first leg 110 and the second leg 120 is directly touching either the right and left lateral walls 30 and 32, respectively, or is directly touching either the anterior and posterior walls 34 and 36, respectively to provide a supportive backdrop for the urethral tube 18. The urethral tube 18 will now be sufficiently compressed to intercept the flow of urine and to provide support to the urinary sphincter muscle 44 so that it can function properly. By permitting the urethral tube 18 to be compressed upon itself between the urinary incontinence device 100 and the symphysis pubis 22, the involuntary flow of urine from the bladder is limited.

Figure 5:
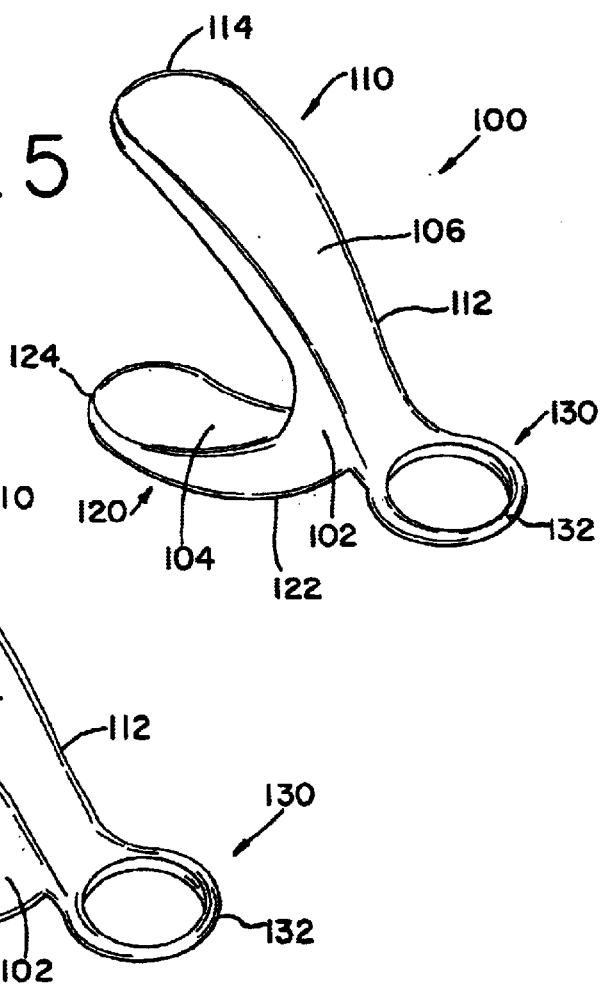
FIG. 5 is a perspective view of one embodiment of the urinary incontinence device of the present invention where the legs of the device are in an upward position when the device is inserted. In other words, the legs are adjacent the cervix when the device is in use.

Referring now to FIG. 5, one embodiment of the urinary incontinence device 100 is shown. The device 100 has a base portion 102 that connects a first leg 110 to a second leg 120 to form a generally "C-shaped" configuration. The device has an inner surface 104 and an outer surface 106 with both of the surfaces having smooth edges and/or contours to minimize any discomfort from the insertion, placement, and withdrawal of the device 100.

Advantageously, the device 100 may be of a unitary construction and may be formed by molding an inert, biocompatible synthetic resin that has a modulus of elasticity. One such resin is a molded silicone compound, polyurethane, or other suitable biocompatible material or a combination of materials. In any event, the device 100 whether made of unitary construction or otherwise, is made of a suitable biocompatible material, which is known to those of skill in the art.

The base portion 102 is formed of a flexible material that biases the legs 110, 120 in an outward direction but is sufficiently resilient to allow the legs 110, 120 to be compressed in a direction toward each other so that insertion of the device 100 is simplified.

The first leg 110 has a proximal end 112 that is connected to the base portion 102 and a distal end 114 extending from the proximal end 112. Likewise, the second leg 120 has a proximal end 122 that is connected to the base portion 102 and a distal end 124 extending from the proximal end 122. Each leg has a length from about 40 mm to about 70 mm, preferably from about 50 mm to about 60 mm, more preferably about 55 mm.

The distal end 114 and 124 present a curved profile so that any discomfort is minimized. Generally, the distal end has a radius of curvature from about 0.125 inch to about 0.9375 inch, preferably from about 0.5625 inch to about 0.8125 inch, more preferably about 0.75.

Figure 6:
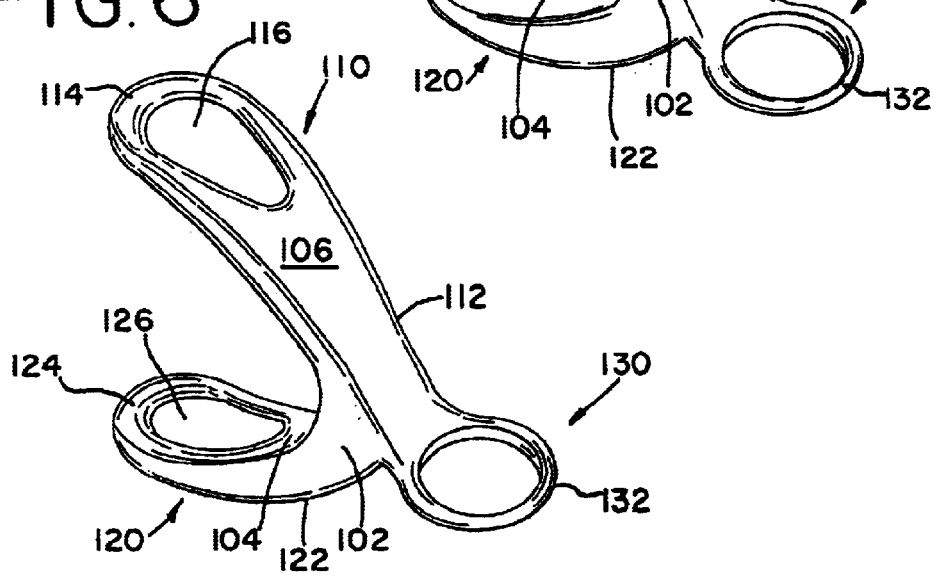
FIG. 6 is a perspective view of another embodiment of the urinary incontinence device of the present invention where the legs of the device are in an upward position when the device is inserted. In other words, the legs are adjacent the cervix when the device is in use.

As shown in FIG. 6, in one embodiment, the distal end 114 of the first leg 110 is provided with an aperture 116 to reduce material costs and to potentially provide greater comfort in use. Likewise in this embodiment, the distal end 124 of the second leg 120 may be provided with an aperture 126.

The device 100 also has a member 130 that can be used to insert the device into the vagina, withdraw the device from the vagina or can be used to do both. In this regard, referring to FIGS. 5 and 6, the member 130 is on the outer surface 106 of the base portion 102 and extends in an outward direction. The member 130 in this embodiment may take any suitable shape but generally has a curved shape to minimize any undue friction or other irritation. The member 130 is shown in FIGS. 5 and 6 as a ring shaped member 132 with a central aperture.

In the embodiment shown in FIGS. 5 and 6, the device 100 is inserted into the vagina 12 such that, in position, the device 100 is downwardly concave with the legs 110, 120 extending upward, as shown in FIG. 1. In addition, the device 100 can be selectively positioned so that the first leg 110 is directly touching the right vaginal wall 30 and the second leg 120 is directly touching the left vaginal wall 32. Alternatively, the device 100 can be selectively positioned so that the first leg 110 is touching the anterior wall 34 and the second leg 120 is touching the posterior wall 36.

Turning now to FIGS. 7–9, other embodiments of the present invention are shown. The device 100 of these embodiments is also a generally "C-shaped" device except that, in use, the device 100 assumes an upwardly convex position with the legs 110, 120 extending downward. Referring specifically to FIG. 7, the device 100 has a member 130 that includes a first removal member 140 in the form of a string that extends from the distal end 114 of the first leg 110 and a second removal member 142 also in the form of a string that extends from the distal end 124 of the second leg 120.

In an alternative embodiment as shown in FIG. 8, the member 130 may include a first removal member 140, a second removal member 142, a first insertion member 144 and a second insertion member 146. The first removal member 140 is in the form of a string that extends from the distal end 114 of the first leg 110. The second removal member 142 is also in the form of a string that extends from the distal end 124 of the second leg 120. The first insertion member 144 extends from the inner surface 104 of the distal end 114 of the first leg 110 and cooperatively engages the second insertion member 146 that extends from the inner surface 104 of the distal end 124 of the second leg 120. As noted, the first insertion member 144 cooperates with the second insertion member 146 to position and hold the distal ends 114, 124 of the legs 110, 120 adjacent each other for insertion of the device 100 into the vagina 12 using a suitable insertion tool (not shown). The insertion tool not only selectively positions the device 100 but also releases the first insertion member 144 from cooperative engagement with the second insertion member 146.

In yet another embodiment as best seen in FIG. 9, the member 130 includes a first insertion member 244 provided on the outer surface 106 of the distal end 114 of the first leg 110. An identical second insertion member (not shown) is likewise provided on the outer surface 106 of the distal end 124 of the second leg 120. An insertion tool (not shown) biases the first leg 110 toward the second leg 120 to present a smaller profile of the device 100 for insertion into the vagina 12. The insertion tool also selectively positions the device 100 and, upon release, the legs 110 and 120 are selectively biased outwardly in contact with the right and left vaginal walls 30, 32 or the anterior and posterior vaginal walls 34, 36.

In yet another alternative embodiment shown in FIG. 10, the member 130 includes a first insertion member 344 provided on the inner surface 104 of the distal end 114 of the first leg 110 and a second insertion member 346 provided on the inner surface 104 of the distal end 124 of the second leg 120. An insertion tool (not shown) biases the first leg 110 toward the second leg 120 to present a smaller profile for insertion of the device 100 into the vagina 12. The insertion tool also selectively positions the device 100 and, upon release, the legs 110 and 120 are selectively biased outwardly in contact with the right and left vaginal walls 30, 32 or the anterior and posterior vaginal walls 34, 36.

Figure 11:
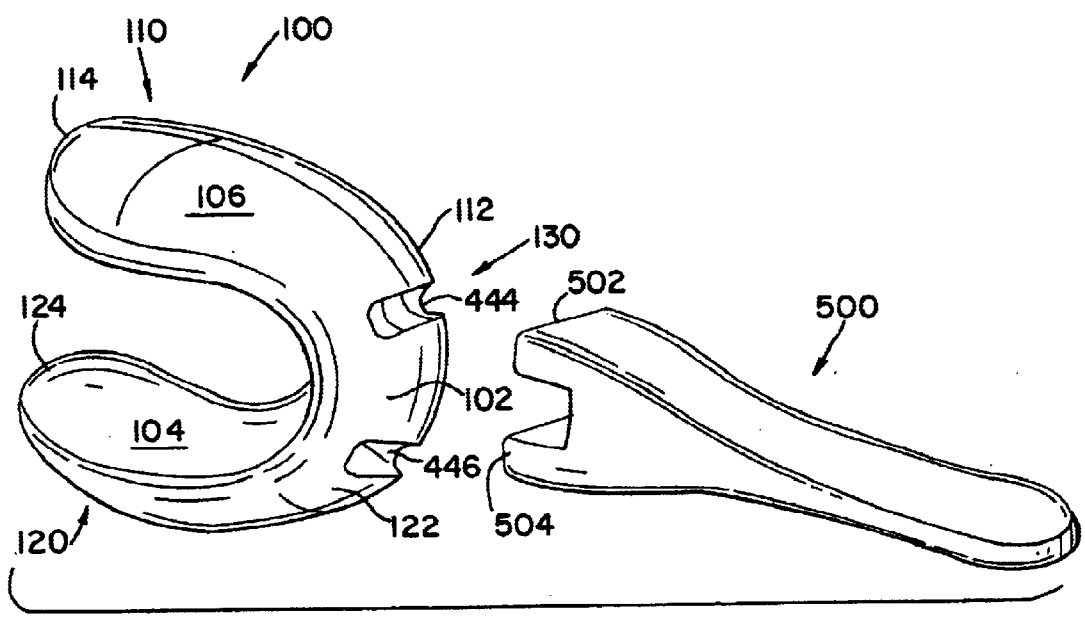
FIG. 11 is a perspective view of another embodiment of the urinary incontinence device of the present invention where the legs of the device are in an upward position when the device is inserted and wherein the device includes a member that includes an insertion and removal member at the proximal end of each leg for cooperating with an insertion apparatus.
Figure 12:
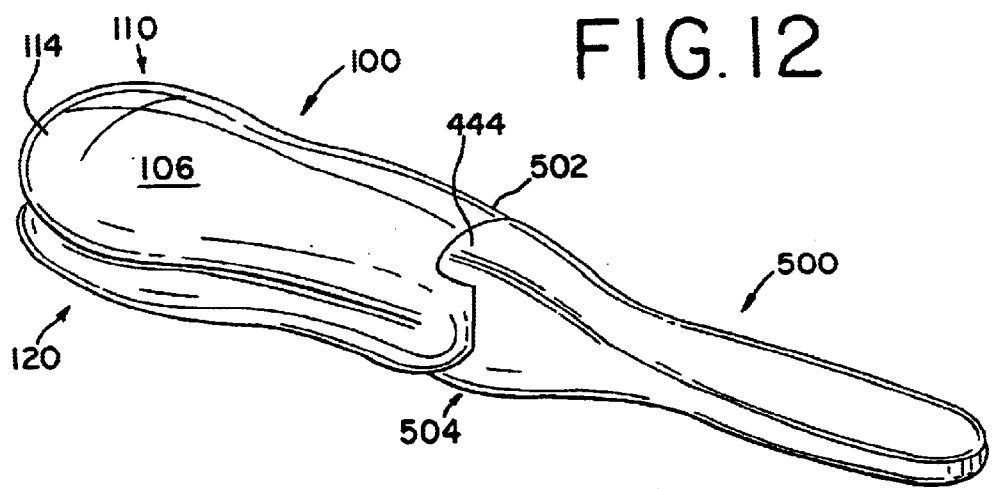
FIG. 12 is a perspective view of the urinary incontinence device embodiment of FIG. 11 where the legs of the device are in an upward position when the device is inserted and wherein the device includes a member that includes an insertion and removal member at the proximal end of each leg that is engaged with an insertion and/or removal apparatus so that the legs are adjacent each other and the device is ready for insertion into a vagina.

Turning now to FIGS. 11 and 12, another embodiment of the urinary incontinence device 100 of the present invention is shown. In this embodiment, the insertion and removal member 130 is provided adjacent the base portion 102. In particular, the insertion and removal member 130 includes a first detent 444 and a second detent 446 respectively provided on the outer surface 106 at the proximal 112, 124 of the legs 110, 120. The detents 444, 446 cooperative with respective flanges 502, 504 provided on an insertion/removal tool 500.

As more particularly shown in FIG. 12, the flanges 502, 504 engage the respective detents 444, 446 to bias the first leg 110 toward the second leg 120 to present a smaller profile of the device 100 for insertion into and removal from the vagina.

The device of the present invention as described above may be disposed after a single use, may be worn more than once, or may be reusable for a period of time (e.g., one week) before being disposed.

While the invention has been described in conjunction with specific embodiments, it is to be understood that many alternatives, modifications, and variations will be apparent to those skilled in the art in light of the foregoing description. Accordingly, this invention is intended to embrace all such alternatives, modifications, and variations that fall within the spirit and scope of the appended claims.

What is claimed:

1. An intra-vaginal urinary incontinence device comprising:
   a. a flexible base portion connecting a proximal portion of a first leg and a proximal portion of a second leg to form a generally "C-shaped" configuration wherein the distal portion of the first leg and the distal portion of the second leg are pointed in the same general direction; and,
   b. a member selected from the group consisting of an insertion member, a removal member, or a combination of both, wherein the member extends from one of the flexible base portion, the distal portion of the first leg, or the distal portion of the second leg.

2. The device of claim 1 wherein the base portion is formed of a resilient material.

3. The device of claim 2 wherein the base portion biases the legs outwardly to aid in retaining the device within the vagina.

4. The device of claim 1 wherein the first leg is adapted to contact an anterior vaginal wall and the second leg is adapted to contact a posterior vaginal wall.

5. The device of claim 1 wherein the first leg is adapted to contact a left vaginal wall and the second leg is adapted to contact a right vaginal wall.

6. The device of claim 1 wherein the device is upwardly convex with the legs extending downward.

7. The device of claim 6 wherein the member comprises a first removal member on a distal portion of the first leg and a second removal member on a distal portion of the second leg.

8. The device of claim 7 wherein the first removal member and the second removal member includes a string.

9. The device of claim 7 wherein the member further comprises a first insertion member on the distal portion of the first leg and a second insertion member on the distal portion of the second leg.

10. The device of claim 1 wherein the device is downwardly concave with the legs extending upward.

11. The device of claim 10 wherein the member is provided on the base portion.

12. An intra-vaginal urinary incontinence device comprising a flexible base portion connecting a proximal portion of a first leg and a proximal portion of the second leg to form a generally "C-shaped" configuration, wherein the distal portion of the first leg and the distal portion of the second leg are pointed in the same general direction, wherein the base portion is formed of a resilient material to bias the legs outwardly to aid in retaining the device within the vagina, wherein the member is selected from the group consisting of an insertion member, a removal member or a combination of both, wherein the member extends from one of the flexible base portion, the distal portion of the first leg, or the distal portion of the second leg.

13. A method of alleviating female urinary incontinence comprising the steps of:
   a. providing an intra-vaginal urinary incontinence device comprising:
      i. a flexible base portion connecting a proximal portion of a first leg and a proximal portion of a second leg to form a generally "C-shaped" configuration wherein the distal portion of the first leg and the distal portion of the second leg are pointed in the same general direction; and,
      ii. a member selected from the group consisting of an insertion member, a removal member, or a combination of both, whereas the member extends from one of the flexible base portion, the distal portion of the first leg, or the distal portion of the second leg;
   b. inserting the device into a woman's vagina while compressing the legs of the device toward each other, wherein the vagina has a vaginal canal with an inner periphery made up of a left wall opposed to a right wall and an anterior wall opposed to a posterior wall; and
   c. allowing the legs of the device to expand within the vaginal canal such that the legs contact two opposed walls.

14. The method of claim 13 further comprising removing the device from the vagina.

15. The method of claim 13 wherein the legs respectively contact the left wall and the right wall.

16. The method of claim 13 wherein the legs respectively contact the anterior wall and the posterior wall.

17. The method of claim 13 wherein the device is inserted such that the legs extend downward.

18. The method of claim 13 wherein the device is inserted such that the legs extend upward.

19. The method of claim 13 wherein the member includes a first member on a distal portion of the first leg and a second member on a distal portion of the second leg.

20. The method of claim 13 wherein the member extends outward from the base portion.

* * * * *